United States Patent [19]

Ferguson et al.

[11] Patent Number: 4,977,140

[45] Date of Patent: Dec. 11, 1990

[54] INJECTABLE SUSTAINED RELEASE FORMULATION

[75] Inventors: Thomas H. Ferguson, Greenfield; Roger G. Harrison, Zionsville; David L. Moore, Indianapolis, all of Ind.

[73] Assignee: Eli Lilly and Company, Indianapolis, Ind.

[21] Appl. No.: 327,861

[22] Filed: Mar. 23, 1989

Related U.S. Application Data

[63] Continuation of Ser. No. 768,605, Aug. 23, 1985, abandoned.

[51] Int. Cl.$^5$ .................. A61K 37/36; C07K 13/00
[52] U.S. Cl. ............................ 514/12; 514/964; 514/965; 530/399
[58] Field of Search ............... 514/12, 964, 965; 530/399

[56]  References Cited

U.S. PATENT DOCUMENTS

| 2,443,778 | 6/1948 | Romansky | 514/192 |
| 2,493,202 | 1/1950 | Macek | 167/82 |
| 4,452,775 | 6/1984 | Kent | 424/19 |

FOREIGN PATENT DOCUMENTS

| 85036 | 8/1983 | European Pat. Off. . |
| 177478 | 4/1986 | European Pat. Off. . |
| 3762 | 10/1950 | Japan . |
| 3098 | 5/1955 | Japan . |
| 1849 | 3/1957 | Japan . |
| 8198 | 9/1957 | Japan . |

OTHER PUBLICATIONS

Davis et al., *J. Dairy Sci.* 66, pp. 1980-1982 (1983), Continuous Elevation of Blood Growth Hormone Concentrations by Beeswax Implant.

Buckwalter, et al., *J. Am. Pharm. Assn.* 47, 661-666 (1958) The Effect of Vehicle and Particle Size on the Absorption, by the Intramuscular Route, of Procaine Pennicillin G Suspensions.

Floyd, *J. Pharm. Pharmacol.* 1, 747-755 (1949) Penicillin Formulations: Efficacy of Oily Injections.

Slevin, et al., *Investigational New Drugs* 2, 271-276 (1984), The Pharmacokinetics of Subcutaneous Bolus Cytosine Arabinoside in an Arachis Oil Plus Aluminum Disearate Suspension.

Davis et al, cited in Chem. Abstracts, vol. 99, 1983 170004r.

*Primary Examiner*—Jacqueline Stone
*Attorney, Agent, or Firm*—Donald R. Stuart; Leroy Whitaker; Joseph Jones

[57] ABSTRACT

A dairy cow injected with a sustained release formulation comprising bovine somatotropin, a wax, and an oil produces more milk for 28 days.

7 Claims, No Drawings

INJECTABLE SUSTAINED RELEASE FORMULATION

RELATED APPLICATION

This application is a continuation of Ser. No. 06/768,605, filed Aug. 23, 1985 now abandoned.

BACKGROUND OF THE INVENTION

This invention belongs to the fields of animal husbandry and pharmaceutical chemistry, and provides a superior sustained release injectable formulation of bovine somatotropin, a polypeptide growth hormone which has long been the subject of research. Its structure and properties are discussed by Wallis and Davies, in Pecile and Muller, Editors, Growth Hormone and Related Peptides, *Excerpta Medica,* Amsterdam, 1967, pp. 1-13.

The earlier work with animal hormones, such as bovine somatotropin, was characterized by difficulty in obtaining amounts of the hormones sufficient for useful experiments. The hormones could be obtained only by isolation from the appropriate glandular tissue of animals, and the procedures were tedious and wasteful in the extreme. See, for example, an article by Reichert on the purification of anterior pituitary hormones, including bovine growth hormone, at page 360-380 of Methods in Enzymology, Vol. 37.

More recently, experimentation in animals with bovine somatotropin has become feasible on a large scale because of the development, by genetic modification methods, of microorganisms which can produce the hormones in vitro.

A number of processes for preparing bovine somatotropin by use of such microorganisms have been published. It should be noted that some of the modified microorganisms produce a modified somatotropin, typically modified by bearing one or a few extra amino acids on an end of the polypeptide chain. According to the literature, these modified hormones have the same properties and activity as does natural bovine somatotropin. Accordingly, throughout this document, the term "bovine somatotropin" is used to include modified bovine somatotropins, synthesized by genetically modified microorganisms, which share the properties and activity of natural bovine somatotropin.

The following group of patent documents and publications describe modified microorganisms, and processes making use of such microorganisms, which synthesize bovine somatotropin.

Mayne, et al., European Patent Publication No. 0095361

George, et al., European Patent Publication No. 0111814

Rottman, et al., European Patent Publication No. 0067026

Miller, et al., European Patent Publication No. 0047600

Frazer, et al., European Patent Publication No. 0068646

Aviv, et al., British Patent Application No. 2073245

De Boer, et al., European Patent Publication No. 0075444

Schoner, et al., *Biotechnology,* Feb. 1985, 151-154

Schoner, et al., *Proc. Nat. Acad. Sci. USA* 81, 5403-07 (1984)

It has been known for more than 35 years that bovine somatotropin, administered to dairy cows, will increase the yield of milk without adversely affecting the composition of it. Cotes, et al., *Nature* 164, 992 (1949). Numerous experiments were carried out, following the work of Cotes and his group, to explore further the relationship between somatotropin and increased milk yield in dairy cattle, and more recently the focus has shifted to experiments with somatotropin produced by genetically modified microorganisms. For example, see Eppard, et al., *Proc. Cornell Nutr. Conf.,* 1984, p. 5. Some workers report that microorganism-synthesized bovine somatotropin is even more effective in increasing milk yield than is the natural hormone. DeGoeter, et al., European Patent Publication No. 0085036.

SUMMARY OF THE INVENTION

The present invention provides to the art an injectable sustained release formulation of bovine somatotropin which comprises an effective concentration of bovine somatotropin suspended in a carrier comprising from about 1% to about 20% of a wax and from about 80% to about 99% of an oil.

DESCRIPTION OF THE PREFERRED EMBODIMENTS

Throughout this document, all expressions of percentage, proportion and the like are in weight units unless otherwise stated.

The wax component of the formulation is preferably chosen from vegetable and animal-origin waxes. For example, useful waxes include esparto wax, Japan wax, jojoba wax, wool wax, spermaceti wax, Chinese wax and, particularly, Carnauba wax and beeswax. Beeswax is readily available in various purification grades; both highly purified white beeswax and the common yellow beeswax of commerce have been successfully used in the present formulations. Further, petroleum waxes, mineral waxes and silicone waxes may be used.

The oil is chosen from the oils which are readily obtainable in a reasonably pure form and which are physiologically acceptable. Of course, the oil must be sufficiently refined that it is stable in storage, does not produce a precipitate upon standing, does not have any observable chemical reactions, and has no observable physiological reactions in the animal to which it is administered. The preferred oils are vegetable oils such as soybean oil, peanut oil, sesame oil, cottonseed oil, corn oil, olive oil, castor bean oil, palm oil, almond oil and the like, particularly peanut oil and sesame oil. Other oils may also be used, including petroleum oils, mineral oils and silicone oils.

The general range of ratios of oil and wax in preparing the carrier is from about 1% to about 20% wax. It is preferred to use from about 5% to about 15% wax, and more preferred to use from about 5% to about 10% wax. In general, the larger the concentration of wax, the longer the sustained action of the formulation. The upper limit on the wax concentration is set by the requirement that the formulation be injectable through a coarse hypodermic needle. While the approximate upper limit on the wax concentration is, as stated, about 20%, the viscosity and injectability of the formulation is affected by a number of factors, particularly the particle size and concentration of the somatotropin and the storage temperature of the formulation. Thus, the upper limit of the wax concentration is not regarded as a precise figure, but as an approximate figure which may be varied somewhat according to the other circumstances of the formulation.

The carrier of the formulation is described as comprising oil and wax. Entirely satisfactory formulations have been prepared without any other ingredient. However, formulations chemists will understand that the addition of relatively minor concentrations of other ingredients could be desirable in some circumstances and would not affect the essence of the present invention. Such minor ingredients could include, for example, dyes, preservatives, antibiotics to combat injection-site infections, viscosity-adjusting agents, or stabilizers and antioxidants to improve the self-life of the formulation. The amounts of such minor ingredients could range from a few hundredths of one percent up to a few percent of the final formulation.

For example, useful dyes include the F D & C dyes and the D & C dyes. Preservatives include benzoic acid, chlorobutanol, potassium sorbate, sorbic acid, sulfur dioxide, propyl gallate, the parabens, ethyl vanillin, glycerin, phenol, parachlorophenol and the like. Viscosity-adjusting agents include, for example, isopropyl myristate, fumed silicon dioxide, sodium alginate, methylcellulose, aluminum monostearate, hexaglycerol distearate, glycerol monostearate and the like. Useful stabilizers include such substances as ethylenediamine and agar. Antioxidants are chosen from such compounds as ascorbyl palmitate, sodium bisulfite, sodium metabisulfite, sulfur dioxide, maleic acid, propyl gallate, sodium formaldehyde sulfoxylate, BHA, BHT, t-butylhydroquinone and the like. All of the above are known to formulation chemists.

The source and type of the bovine somatotropin used in the present formulations is not significant. Natural somatotropin obtained from animals may be used, or any of the types of microorganism-origin somatotropin may be used, depending on convenience and economics. The physical properties of both natural and microorganismorigin bovine somatotropin are equally desirable for use in the present formulation. Accordingly, any bovine somatotropin is an appropriate active ingredient for use in the present formulations.

An effective concentration of bovine somatotropin is combined with the carrier to prepare the formulation. The concentration depends upon the length of the desired sustained release action, and also upon the dose be administered. It is necessary, of course, to take into account the purity or potency of the available somatotropin.

It has been found that injections in the range of 2-10 grams of formulation per dairy cow provide sustained release over a conveniently long period of time, and that such amounts are not so large as to cause inconvenience to the administrator or discomfort to the cow. The concentration of somatotropin in a formulation to be administered in such amounts is in the range of from about 5% to about 35%, preferably in the range from about 10% to about 25%.

The carrier for the present formulation is prepared by dissolving the wax in the oil with heating as necessary. Any minor ingredients which may be used are also conveniently added while the mixture is hot. When the mixture is cooled, its viscosity increases sharply as the wax, at least in part, comes out of solution. It is preferred to homogenize the carrier after it has cooled to approximately ambient temperature to reduce the particle size of the wax and thereby reduce the viscosity of the mixture. The usual types of equipment are effective. For example, one can use a machine which forces the mixture through a fine orifice under high pressure, or a high-intensity mixer which uses a high-speed agitator closely enveloped by a baffled stator to provide intense shear. Many types of equipment are available, under many trade names, and any equipment which provides high-shear mixing will suffice.

It is preferred to provide the bovine somatotropin in the form of a fine powder, and to mix it relatively gently with the homogenized carrier. Since the product is injectable, the particle size of the somatotropin must be small enough to pass easily through hypodermic needles. It is advisable to mix the somatotropin with the carrier by means of gentle stirring, such as a propeller agitator or the like, but it may be possible to use high-energy mixing after the somatotropin has been added, if great care is taken to avoid localized heating and excessive shear of the mixture as it passes through the high-energy part of the mixer.

The examples below illustrate excellent sustained release administration of bovine somatotropin over periods of about 28 days. It is believed that a 28-day interval between injections, or even a longer interval as appears possible within the concept of the present invention, is convenient and economical, and accordingly that the present formulation provides a very superior way to administer bovine somatotropin.

The following specific examples of sustained release formulations according to the present invention are provided to assure that the reader fully understands the invention and how to make its formulations.

EXAMPLE 1

Eighteen hundred g of sesame oil was heated to about 100° C., and two hundred g of refined white beeswax was added. The mixture was stirred at constant temperature until the wax dissolved into the oil, and the mixture was then cooled, with constant mild agitation, to about 22° C. The oil-wax mixture was then homogenized with an Ultra-Turrax homogenizer until the mixture had become smooth and creamy in consistency, and its viscosity had been reduced.

To a 13.16 g portion of the above oil-wax mixture was added, with gentle agitation at 22° C., 2.83 g of bovine somatotropin, synthesized by a modified *Escherichia coli* culture as described in European Patent Publication No. 0095361. The preparation of somatotropin was quite pure, containing about 75% of total protein, as determined by optical density measurement of solubilized material, of which about 95% was monomeric bovine somatotropin and related substances as determined by size exclusion chromatography. The formulation contained about 12.6% of bovine somatotropin and related substances.

EXAMPLES 2-7

The following examples were prepared substantially as described in Example 1. The compositions of them will be tabulated for convenience.

| Carrier | % Somatotropin |
| --- | --- |
| 2. 95%/5% sesame oil/white beeswax | 12.4 |
| 3. 90%/10% peanut oil/yellow beeswax | 12.6 |
| 4. 99%/1% peanut oil/yellow beeswax | 12.6 |
| 5. 99%/1% peanut oil/yellow beeswax | 12.6 |
| 6. 99%/1% peanut oil/yellow beeswax | 10.9 |
| 7. 90%/10% peanut oil/yellow beeswax | 12.6 |
| 8. 90%/10% silicone (polydimethyl- | 12.6 |

| Carrier | % Somatotropin |
|---|---|
| siloxane) oil, medical grade 350 cs/silicone wax (stearoxy trimethylsilane-stearyl alcohol) | |
| 9. 90%/10% [same as Ex. 8 but food grade silicone oil] | 12.6 |
| 10. 90%/10% silicone (polyphenyl-methylsiloxane copolymer, 22.5 cs) oil/silicone wax (stearoxy trimethylsilane-stearyl alcohol) | 12.6 |

EXAMPLES 8–26

The following group of examples, which are also made in the same manner described in Example 1, illustrate further embodiments of the invention.

| | Carrier | % Somatotropin |
|---|---|---|
| 11. | 90%/10% peanut oil/yellow beeswax | 15 |
| 12. | 95%/5% peanut oil/white beeswax | 6 |
| 13. | 95%/5% peanut oil/Carnauba wax | 35 |
| 14. | 87%/13% soybean oil/Carnauba wax | 27 |
| 15. | 85%/15% sesame oil/yellow beeswax | 9 |
| 16. | 97%/3% cottonseed oil/white beeswax | 5 |
| 17. | 92%/8% cottonseed oil/Carnauba wax | 18 |
| 18. | 85%/15% soybean oil/yellow beeswax | 22 |
| 19. | 80%/20% jojoba oil/silicone wax | 30 |
| 20. | 82%/18% palm oil/petroleum wax | 25 |
| 21. | 95%/5% silicone oil/Carnauba wax | 20 |
| 22. | 93%/7% olive oil/beeswax | 17 |
| 23. | 98%/2% corn oil/jojoba wax | 32 |
| 24. | 89%/11% almond oil/esparto wax | 24 |
| 25. | 86%/14% castor bean oil/Japan wax | 14 |
| 26. | 83%/17% mineral oil/wool wax | 16 |

EXAMPLE 27

| Carrier | |
|---|---|
| 89.80% | sesame oil |
| 9.98 | white beeswax |
| 0.02 | propyl gallate |
| 0.18 | methylparaben |
| 0.02 | propylparaben |

The ingredients were combined, heated to about 125° C., and cooled to room temperature. The cooled mixture was homogenized as described in Example 1, and cooled to room temperature. To 82 parts by weight of the carrier was added, with gentle stirring, 18 parts by weight of the bovine somatotropin preparation described in Example 1, resulting in a formulation containing 12.8% of bovine somatotropin and related substances.

TEST 1

Compositions of the present invention were tested in lactating Holstein cows which were averaging about 56 pounds per day of milk when the test began. A test group and a control group of 7 cows each were used. One control cow had to be removed because of hardware disease, and 2 treated cows were removed from the test because of hardware disease and mastitis, respectively. The cows were housed in a large tie stall barn, and were given two hours of outdoor exercise each day, while the stalls were cleaned and rebedded.

The cows were fed ad lib on a diet consisting of 60% forage (3 parts of corn silage and 1 part chopped alfalfa hay), and 40% concentrate, all on a dry matter basis. The concentrate portion of the feed had the following composition.

| Ingredient | Percentage |
|---|---|
| dried beet pulp | 10.00% |
| cracked corn | 48.50 |
| soybean oil meal | 33.10 |
| limestone | 1.65 |
| cane molasses | 3.50 |
| monosodium phosphate | 1.05 |
| vitamin A, D3 and E premix | 0.35 |
| selenium premix | 0.05 |
| sodium bicarbonate | 0.75 |
| trace element salts | 1.05 |

The cows were milked twice daily, at intervals of about 11 and 13 hours. The production of milk was recorded and samples of the milk were analyzed by conventional procedures.

After a 14-day conditioning period, the treatment group of cows was injected subcutaneously with an 7.3 g depot injection of the formulation of Example 6, which was injected through 14-gauge needles. On the 29th day after the first injection, the animals were administered a 7.3 g injection of the formulation of Example 7, and a third injection of 7.3 g of the formulation of Example 7 was administered on the 57th day after the first injection.

Thus, the experiment consisted of three 28-day sustained release periods.

The release of somatotropin from the depot injections was followed by measuring the concentration of bovine somatotropin in the plasma of the treated cows. Blood samples were taken by puncture of the jugular or coccygeal vein on Mondays and Fridays of each week, and the samples were analyzed by double antibody radioimmunoassay.

The results obtained over the three periods of 28 days each have been averaged to prepare the following table, where the average analyses are presented as nanograms/ml of bovine somatotropin. The control results are not tabulated, since those results all fell in a very narrow range from 2.9 to 3.3 ng/ml at all times.

| Day | Somatotropin Concentration |
|---|---|
| 2 | 128 ng/ml |
| 5 | 171 |
| 9 | 109 |
| 12 | 86 |
| 16 | 54 |
| 19 | 43 |
| 23 | 27 |
| 26 | 20 |

As would have been expected from the excellent delivery of somatotropin, the milk production of the treated cows was significantly increased and the composition of their milk was normal.

TEST 2

In this test, treatment and control groups of three cows each were used. The cows were managed and fed essentially as described in Test 1 above, and the results were measured by analyzing blood plasma levels of somatotropin in the same manner as in Test 1. The test was followed for 29 days after administering a depot injection of 7.3 g of the formulation of Example 5 to each cow. The following results were obtained. In this test, there was considerable variability in the somatotropin levels in the control cows, so the control data is shown here.

| Day | Somatotropin Concentration | |
|---|---|---|
| | Control | Treatment |
| 0 | 5 ng/ml | 6 ng/ml |
| 2 | 9 | 225 |
| 4 | 7 | 106 |
| 6 | 10 | 81 |
| 8 | 20 | 50 |
| 10 | 17 | 49 |
| 12 | 14 | 47 |
| 14 | 15 | 38 |
| 16 | 13 | 34 |
| 18 | 8 | 25 |
| 20 | 18 | 31 |
| 22 | 10 | 17 |
| 24 | 6 | 21 |
| 29 | 7 | 17 |

TEST 3

A further test was carried out, substantially as described in Test 1, except that each group consisted of only three cows. There was no control group, but pretreatment samples were taken and analyzed to provide a control for the experiment. The formulations of Examples 1, 2 and 3 were used, and each animal was injected with a 4.9 g depot injection of the proper formulation on day of the experiment.

Samples of the animals' blood were taken on various days through the experiment, and were analyzed for bovine somatotropin with the following results.

| Day | Somatotropin Concentration | | |
|---|---|---|---|
| | Ex. 1 | Ex. 2 | Ex. 3 |
| −5 | 2.9 ng/ml | 3.6 ng/ml | 3.3 ng/ml |
| −2 | 2.3 | 1.2 | 1.6 |
| 1 | 43 | 56 | 42 |
| 2 | 42 | 82 | 53 |
| 3 | 64 | 106 | 81 |
| 4 | 74 | 109 | 76 |
| 5 | 104 | 156 | 93 |
| 9 | 182 | 181 | 172 |
| 12 | 141 | 112 | 124 |
| 16 | 89 | 65 | 82 |
| 19 | 71 | 49 | 64 |
| 23 | 47 | 30 | 42 |
| 26 | 40 | 22 | 30 |

We claim:

1. A method for obtaining 28 days of increased daily milk production from a dairy cow which comprises injecting the cow with 2 to 10 grams of a formulation comprising 10–25% bovine somatotropin suspended in a carrier that comprises 8–20% of a wax and 80–92% of an oil.
2. The method of claim 1 wherein the oil is a vegetable oil.
3. The method of claim 2 wherein the oil is peanut or sesame oil.
4. The method of claim 1 wherein the wax is beeswax.
5. The method of claim 4 wherein the oil is peanut or sesame oil.
6. The method of claim 5 wherein the formulation contains about 10% wax.
7. The method of claim 1 wherein the formulation contains about 10% wax.

* * * * *